United States Patent [19]

Ebeling et al.

[11] 4,136,691

[45] Jan. 30, 1979

[54] RESPIRATION MASK

[75] Inventors: Olavi A. Ebeling; Risto W. Lundén, both of Helsinki, Finland

[73] Assignee: Oy Kontekla, Helsinki, Finland

[21] Appl. No.: 785,844

[22] Filed: Apr. 8, 1977

[30] Foreign Application Priority Data

Apr. 30, 1976 [FI] Finland .................................. 761218

[51] Int. Cl.² ........................................... A61M 16/00
[52] U.S. Cl. .................................................... 128/212
[58] Field of Search ............... 128/212, 186, 192, 147, 128/146 R, 146.3, 146.6

[56] References Cited

U.S. PATENT DOCUMENTS 3,747,598  7/1973  Cowans ............................ 128/142 R

FOREIGN PATENT DOCUMENTS 2436436  3/1975  Fed. Rep. of Germany ........... 128/212
2403359  10/1976  Fed. Rep. of Germany ........... 128/212

Primary Examiner—Henry J. Recla
Attorney, Agent, or Firm—Cushman, Darby & Cushman

[57] ABSTRACT

A respiration mask comprising a mask portion and a heat exchanger through which inhalation and exhalation air flows for the recovery of humidity and humidity contained in the exhalation air. The heat exchanger consists a continuous strip of wire netting wound helically to form a cylindrical netting roll comprising several turns. The flow of air takes place radially through the netting roll.

4 Claims, 4 Drawing Figures

U.S. Patent
Jan. 30, 1979
4,136,691
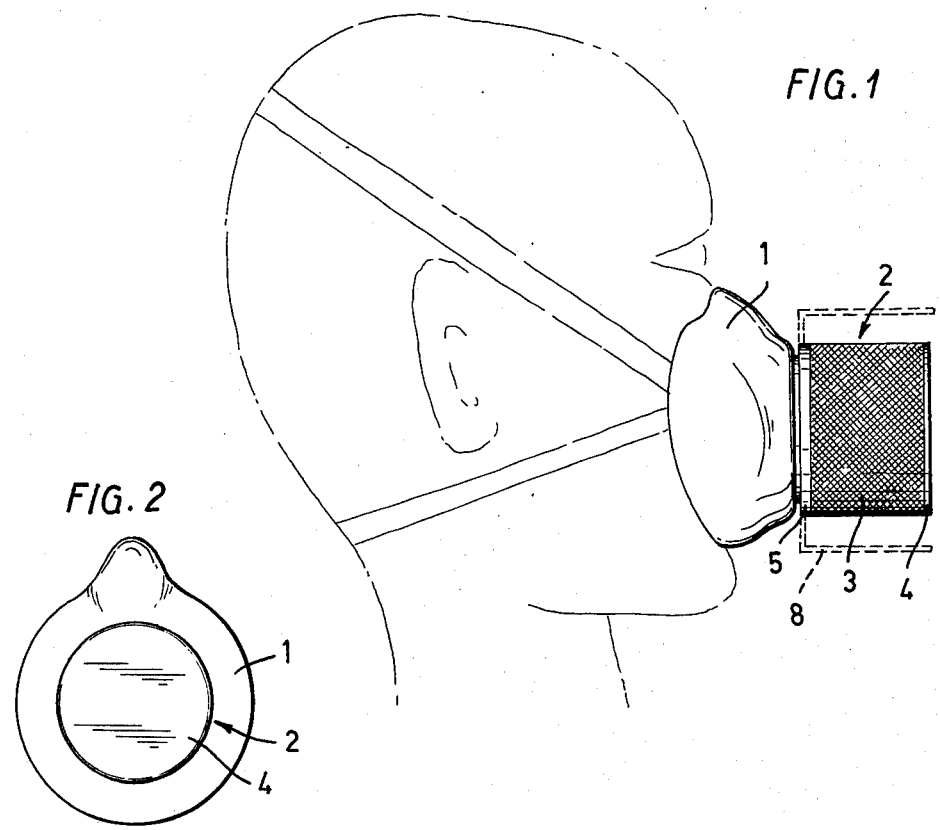
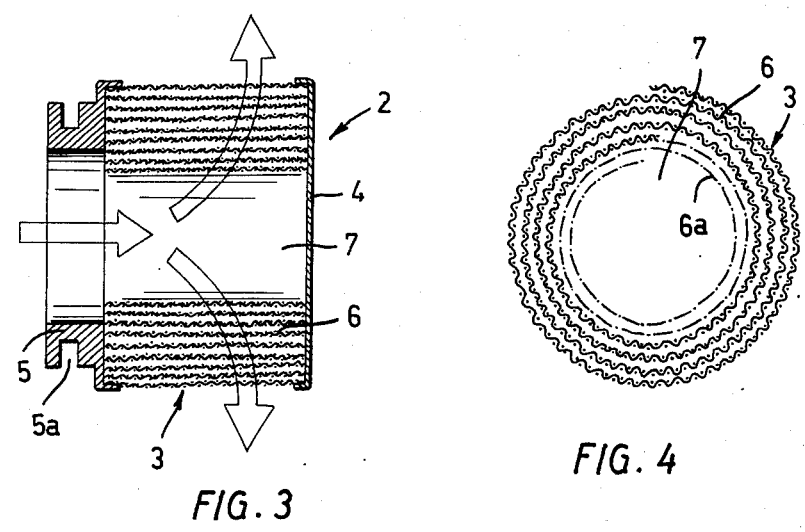

RESPIRATION MASK

This invention relates to a respiration mask comprising a mask portion covering the mouth and nose of a person and a heat exchanger fastened to the mask portion, through which heat exchanger inhalation and exhalation air flows for the recovery of the heat and humidity contained in the exhalation air and for the transfer thereof to the inhalation air, said heat exchanger consisting of a pile of superimposed woven wire nettings detachably fastened to the mask portion, inhalation and exhalation air flowing through the meshes of said wire nettings alternately in opposite directions.

Respiration masks of this kind are previously known intended to be used when working in frosty winter conditions or generally when staying in cold conditions. The respiration mask enables the recovery of heat from the exhalation air and the transfer thereof to the inhalation air. Similarly, the humidity in the exhalation air can be transferred back to the air to be inhaled. By using a heat exchanger composed of wire netting the throughflow resistance is made so small that respiration is not notably hampered even when working. The flow of air through the pile of wire nettings thus takes place both during inhalation and exhalation through the same passages so that the heat exchanger operates as a counterflow generator.

It is previously known to assemble a heat exchanger of several superimposed separate rectangular wire netting sheets joined together to a pile, which is fixed to the respiration opening in the mask portion. The manufacture of such a heat exchanger is, however, difficult because the wire netting has to be cut into separate sheets, which are easily unraveled and which must be assembled to a precise pile. The biggest disadvantage of the heat exchanger is, however, the fact that the outer dimensions of the netting pile vary depending on the number of layers the pile in each particular instance contains. Netting piles intended for different working and climate conditions therefore have different thicknesses and require either mask portions of different sizes or different nests, in which piles of different heights fit and which are detachably fastened to the mask portion.

The object of this invention is a respiration mask eliminating the above mentioned disadvantages, and this object is accomplished with the respiration mask according to the invention, wherein the heat exchanger consists of a continuous strip of wire netting wound helically to a cylindrical netting roll comprising several turns, said netting roll at one axial end being connected to a respiration opening in the mask portion and at the other end being closed so that the flow of air takes place radially through the netting roll.

In the respiration mask according to the invention only one single netting strip is needed, which can be easily rolled up to a roll having the desired outer diameter. The manufacture is hereby considerably simplified. By closing the other end of the cylindrical roll thus obtained and by using the other end as an inflow and outflow opening for air all the air can pass radially through the netting layers of the roll whereby an empty axial space is left in the middle of the roll. The turns need therefore not be wound up so tightly that also the centre of the roll is filled with netting which would be necessary, if the air would pass through the netting roll axially from one end of the roll to the other. The biggest advantage is, however, to be seen in that said empty space in the middle of the roll can be utilized to receive additional turns resulting from the elongation of the netting strip whereby the outer diameter of the roll remains constant. Accordingly, heat exchanger rolls intended for different working and climate conditions and having a different number of wire netting turns can be provided with the same outer dimensions which also simplifies the means needed to close the ends of the rolls and to fix the rolls to the mask portion.

The invention will now be described in more detail in the following with reference to the accompanying drawing, wherein FIGS. 1 and 2 are side and front views, respectively, of one preferred embodiment of the respiration mask according to the invention, FIG. 3 is an axial section of the heat exchanger capsule, and FIG. 4 is a schematic cross-section of the heat exchanger capsule at right angles to the axis thereof.

The respiration mask shown in the drawing comprises a mask portion 1 made of rubber or similar material which is flexible at least at the edges, said mask portion covering the mouth and nose of the person using it and a heat exchanger capsule 2 being fastened thereto.

The heat exchanger capsule consists of a wire netting roll 3 and a closing plate 4 fixed to the other end thereof and an annular fastener 5 fixed to the other end thereof. The roll 3 consists of a continuous narrow wire netting strip 6 wound up to a spiral comprising several turns and having a hollow axial central space 7. The closing plate 4 and the fastener 5 are preferably fastened to the roll 3 by means of vulkanization. The fastener has a peripheral groove 5a, wherein the peripheral edge of the circular respiration opening in the mask portion can be detachably fitted.

During inhalation and exhalation, the air flows axially through the other end of the netting roll and radially through the mantle layers of the netting roll.

As can best be seen from FIG. 4, the hollow axial space 7 in the netting roll allows the elongation of the wire netting strip 6 without having to enlargen the outer diameter of the roll, because the additional turns 6a resulting from the elongation of the strip are received in said axial space. Accordingly, heat exchange capsules intended for different conditions can be given the same outer dimensions and still be provided with the number of netting turns required by the conditions of use in question.

When necessary, the heat exchanger capsule 2 can be encircled by a casing 8 open on one side to eliminate the effect of the wind.

According to one embodiment, the axial length of the netting roll 3 is 21 mm and the outer diameter 50 mm and the roll has abt. 27 turns all composed of one single continuous wire netting strip. The diameter of the netting wires is 0.22 mm and the mesh size is 0.9 × 0.9 mm. The wires are of stainless steel (Aisi 316, Mo content 2,5%).

The drawing and the accompanying specification are only intended to illustrate the idea of the invention. In its details the respiration mask according to the invention may vary considerably within the scope of the claims. Instead of keeping the outer diameters of rolls intended for different conditions constant and instead of receiving the additional turns resulting from the elongation of the netting strips in the empty space in the middle of the rolls, as described above, it is possible to keep the inner diameter of the rolls constant and to let the outer diameters vary depending on the length of the netting strips. It is also possible to use a combination of these two embodiments. The respiration mask may of course be used also in hot ambient conditions such as tropic areas, hot air drying channels etc. to cool the inhalation air.

What we claim is:

1. A respiration mask comprising a mask portion for covering the mouth and nose of a person, said mask portion having a respiration opening therein, and a heat exchanger through which inhalation and exhalation air flows for the recovery of the heat and humidity contained in the exhalation air and for the transfer thereof to the inhalation air, said heat exchanger including a pile of superimposed woven wire nettings formed from at least one continuous strip of wire netting wound helically to form a cylindrical netting roll comprising several turns, said netting roll at one axial end being connected to said respiration opening in the mask portion and means closing the other end of said roll so that the flow of air takes place radially through the netting roll in alternately opposite directions during inhalation and exhalation.

2. A respiration mask as claimed in claim 1, wherein an empty axial space is formed inside the netting roll, said space accomodating additional turns resulting from an elongation of the wire netting strip.

3. A respiration mask as claimed in claim 1 wherein said one end of the netting roll is provided with an annular fastener detachably connected to the mask portion at the location of said respiration opening.

4. A respiration mask as claimed in claim 1 wherein said means closing said other end of the netting roll includes a closing plate fastened by means of vulkanization to the outer edges of the netting turns.

* * * * *